US011771025B2

(12) United States Patent
Charling et al.

(10) Patent No.: US 11,771,025 B2
(45) Date of Patent: Oct. 3, 2023

(54) SYSTEM AND METHOD FOR ADJUSTING IRRIGATION SYSTEM SCHEDULING BASED ON ESTIMATED SOIL WATER DEPLETION

(71) Applicant: LINDSAY CORPORATION, Omaha, NE (US)

(72) Inventors: Kurtis Arlan Charling, Elkhorn, NE (US); Chengchou James Han, Omaha, NE (US)

(73) Assignee: LINDSAY CORPORATION, Omaha, NE (US)

( * ) Notice: Subject to any disclaimer, the term of this patent is extended or adjusted under 35 U.S.C. 154(b) by 747 days.

(21) Appl. No.: 16/684,884

(22) Filed: Nov. 15, 2019

(65) Prior Publication Data

US 2020/0163293 A1   May 28, 2020

Related U.S. Application Data

(60) Provisional application No. 62/771,346, filed on Nov. 26, 2018.

(51) Int. Cl.
*A01G 25/16* (2006.01)
*G05B 19/41* (2006.01)
(Continued)

(52) U.S. Cl.
CPC ......... *A01G 25/167* (2013.01); *A01G 25/092* (2013.01); *G01N 33/246* (2013.01);
(Continued)

(58) Field of Classification Search
CPC .... A01G 25/16; A01G 25/162; A01G 25/165; A01G 25/167; A01G 25/092;
(Continued)

(56) References Cited

U.S. PATENT DOCUMENTS 9,880,537 B2 * 1/2018 Mewes ................. A01G 25/16
2012/0290140 A1 * 11/2012 Groeneveld ........... A01G 22/00
700/284
(Continued)

FOREIGN PATENT DOCUMENTS

WO   WO 2017/133625 A1 *  8/2017  ............. A01G 25/16

OTHER PUBLICATIONS

Machine translation of WO 2017/133625 A1 (Aug. 2017).*
(Continued)

*Primary Examiner* — M. N. Von Buhr
(74) *Attorney, Agent, or Firm* — HOVEY WILLIAMS LLP

(57) ABSTRACT

An irrigation system and method of controlling operations of the irrigation system are provided. The method includes determining, via a control system, a soil water depletion at a first location based on soil data captured via a sensor; determining, via the control system, a difference in irrigation amounts at the first location and a second location; determining, via the control system, a difference in precipitation amounts at the first location and the second location; determining, via the control system, a difference in evapotranspiration values of crops at the first location and the second location; calculating an estimated soil water depletion at the second location based, at least in part, on the soil water depletion at the first location, the difference in irrigation amounts at the first location and the second location, the difference in precipitation amounts at the first location and the second location, and the difference in evapotranspiration values of crops at the first location and the second location; and directing, via the control system, the irrigation system to apply an amount of water at the second location based, at least in part, on the estimated soil water depletion at the second location. The irrigation system may comprise a
(Continued)

fluid-carrying conduit, a plurality of support towers with one or more controllable motors, water emitters, a controllable valve, and a control system that performs one or more of the aforementioned method steps.

20 Claims, 3 Drawing Sheets

(51) Int. Cl.
    *G01N 33/24*     (2006.01)
    *G05B 13/02*     (2006.01)
    *A01G 25/09*     (2006.01)

(52) U.S. Cl.
    CPC .......... *G05B 13/028* (2013.01); *G05B 19/41* (2013.01); *G01N 2033/245* (2013.01); *G05B 2219/2625* (2013.01)

(58) Field of Classification Search
    CPC ...... G05B 13/028; G05B 15/02; G05B 19/41; G05B 19/4103; G05B 19/4105; G05B 19/042; G05B 2219/2625; G01N 33/246; G01N 2033/245; A01C 21/0007; A01C 23/0007; Y02A 40/22; Y02A 40/10; Y02A 20/411; Y10T 137/1866; Y10T 137/189

See application file for complete search history.

(56) References Cited

U.S. PATENT DOCUMENTS

| | | |
|---|---|---|
| 2015/0061888 A1 | 3/2015 | Lankford et al. |
| 2016/0055593 A1* | 2/2016 | Groeneveld ........... G06Q 40/08 705/4 |
| 2016/0227717 A1 | 8/2016 | Wolgast |
| 2016/0366841 A1 | 12/2016 | Wilson |
| 2018/0014452 A1* | 1/2018 | Starr .................... A01C 21/007 |
| 2018/0181893 A1* | 6/2018 | Basso .............. G06Q 10/06313 |
| 2018/0184600 A1 | 7/2018 | Charling et al. |
| 2018/0315100 A1 | 11/2018 | Magnusson et al. |
| 2019/0017984 A1* | 1/2019 | Fang ...................... G01N 27/04 |
| 2019/0208720 A1* | 7/2019 | Nguyen ................. A01G 25/16 |
| 2019/0254242 A1* | 8/2019 | Allen .................... A01G 25/167 |
| 2021/0018484 A1* | 1/2021 | Liu ....................... G01N 33/246 |
| 2021/0059136 A1* | 3/2021 | Hill ....................... A01G 25/167 |
| 2021/0127605 A1* | 5/2021 | Aughton .............. G01N 27/048 |

OTHER PUBLICATIONS

International Search Report and Written Opinion for PCT Appln. No. PCT/US20119/062100; Filed Nov. 19, 2019 and all references cited therein.

\* cited by examiner

SYSTEM AND METHOD FOR ADJUSTING IRRIGATION SYSTEM SCHEDULING BASED ON ESTIMATED SOIL WATER DEPLETION

RELATED APPLICATIONS

The present non-provisional patent application claims priority to U.S. Provisional Patent Application Ser. No. 62/771,346 filed on Nov. 26, 2018, and entitled "SYSTEM AND METHOD FOR ADJUSTING IRRIGATION SYSTEM SCHEDULING." The entirety of the above-identified patent application is hereby incorporated by reference into the present non-provisional patent application.

BACKGROUND

Sensors are often used for irrigation scheduling. For example, sensors are often used to capture information about portions of a field, such as soil moisture to determine how much water to apply to the field. However, there are major limitations to using sensor-based irrigation. One sensor can only measure, for example, the soil moisture of one spot of a single field. Agricultural operations often include several large fields, and several sensors are therefore required to be installed at multiple locations in a single field to obtain sufficient data about the individual field. Moreover, additional sensors may be required to account for spatial variation of the field including soil zone variations, crop zone/management variations, and irrigation zone variations, etc.

Additionally, sensor-based irrigation does not meet the need of modern variable rate irrigation (VRI) technology, which requires data about an entire zone in a field to provide an irrigation prescription for that zone. One or multiple sensors can only cover limited portions of an irrigation zone but cannot cover the entire zone.

Further, the installation and management costs of sensors, including labor costs, sensor prices, installation time, utility accessory (e.g. data logger), and management costs and time, are high. This hinders scaling such technology to relatively large irrigation productions with multiple fields because sensor-based irrigation management would require at least three sensors to properly manage a center pivot field.

The background discussion is intended to provide information related to the present invention which is not necessarily prior art.

SUMMARY

The present invention solves the above-described problems and other problems by providing an irrigation system and methods of controlling operations thereof that greatly reduce the number of sensors required to collect data in a field.

A computer-implemented method of controlling operations of an irrigation system according to an embodiment of the present invention broadly comprises determining, via a control system, a soil water depletion at a first location in a field based on soil data captured via a sensor; determining, via the control system, a difference in irrigation amounts at the first location and a second location; determining, via the control system, a difference in precipitation amounts at the first location and the second location; and determining, via the control system, a difference in evapotranspiration values of crops at the first location and the second location.

The method further comprises calculating an estimated soil water depletion at the second location based, at least in part, on the soil water depletion at the first location, the difference in irrigation amounts at the first location and the second location, the difference in precipitation amounts at the first location and the second location, and the difference in evapotranspiration values of crops at the first location and the second location; and directing, via the control system, the irrigation system to apply an amount of water at the second location based, at least in part, on the estimated soil water depletion at the second location.

By determining some of the relevant differences between attributes of the first location where the sensor may be located and a different location, valuable information can be gleaned about the other location, without requiring additional sensors. The information can then be used to interpolate information about an entire zone. Thus, the information can then be automatically used by the control system to, for example, adjust water application operations. The interpolated information enables the use of variable rate irrigation technology without numerous costly sensors.

An irrigation system constructed in accordance with another embodiment of the present invention utilizes the above-described principles and comprises a plurality of motor-driven mobile support towers configured to move across a field, a fluid-carrying conduit supported above the field by the mobile towers, water emitters coupled with the fluid-carrying conduit, at least one valve for controlling flow of fluids through the water emitters, a sensor configured to capture soil data at a first location in the field, and a control system for controlling the mobile towers and valves to apply specified amounts of water on the field.

The control system is configured to determine a soil water depletion at the first location in the field based on the soil data; determine a difference in irrigation amounts at the first location and a second location; determine a difference in precipitation amounts at the first location and the second location; determine a difference in evapotranspiration values of crops at the first location and the second location; calculate an estimated soil water depletion at the second location based, at least in part, on the soil water depletion at the first location, the difference in irrigation amounts at the first location and the second location, the difference in precipitation amounts at the first location and the second location, and the difference in evapotranspiration values of crops at the first location and the second location; and control operation of the motor and/or the valve to apply an amount of water at the second location based, at least in part, on the estimated soil water depletion at the second location.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present invention will be apparent from the following detailed description of the embodiments and the accompanying drawing figures.

BRIEF DESCRIPTION OF THE DRAWING FIGURES

Embodiments of the present invention are described in detail below with reference to the attached drawing figures, wherein.

Figure 1:
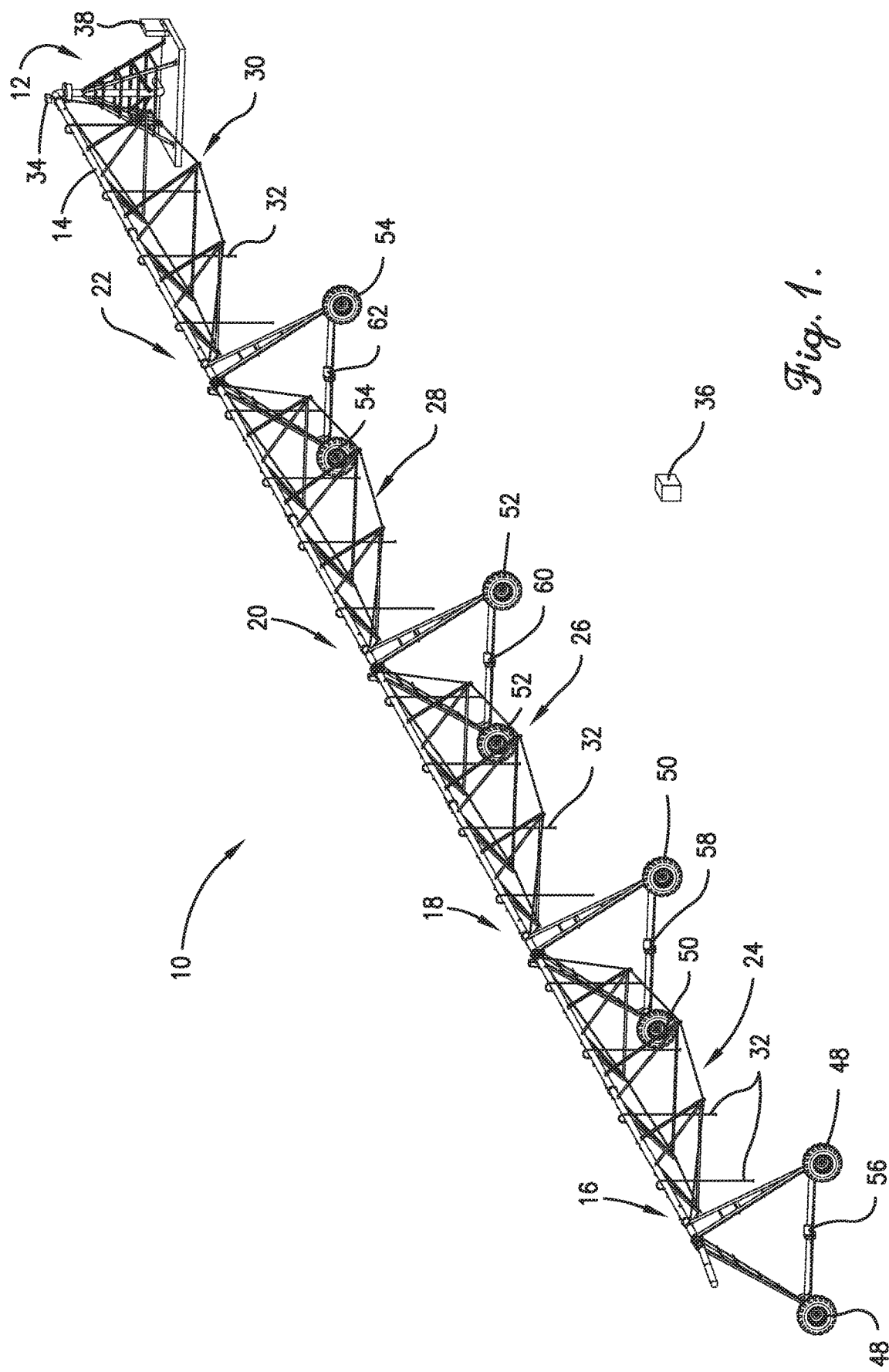
FIG. 1 is a perspective view of an exemplary irrigation system with which principles of the present invention may be implemented.

The drawing figures do not limit the present invention to the specific embodiments disclosed and described herein. The drawings are not necessarily to scale, emphasis instead being placed upon clearly illustrating the principles of the invention.

DETAILED DESCRIPTION OF THE EMBODIMENTS

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the present technology can include a variety of combinations and/or integrations of the embodiments described herein.

Turning to FIG. 1, an irrigation system 10 constructed in accordance with an embodiment of the invention is illustrated. The illustrated irrigation system 10 is a pivot irrigation system, but can be any other irrigation system, such as a lateral irrigation system. The irrigation system 10 may have access to a hydrant, well, water tank, or other source 12 of water and may also be in fluid communication with a tank or other source of agricultural products to inject fertilizers, pesticides and/or other chemicals into the water for application during irrigation.

The irrigation system 10 may comprise a number of spaced-apart mobile towers 16, 18, 20, 22, a fluid-distribution conduit 14 in fluid communication with the water source 12 and supported by the towers 16, 18, 20, 22 above a field, a plurality of truss sections 24, 26, 28, 30 or other supports to form a number of interconnected spans that help support the conduit 14, a plurality of fluid emitters 32 that are in fluid communication with the conduit 14, one or more valves 34 for controlling flow of fluids to the emitters 32, one or more sensors 36 for capturing data about the field, and a control system 38 for controlling operation of the irrigation system 10.

The mobile towers 16, 18, 20, 22 support the conduit 14 and carry the conduit 14 and emitters 32 across the field. Each mobile tower 16, 18, 20, 22, includes a frame 40, 42, 44, 46 for supporting a portion of the conduit 14 and wheels 48, 50, 52, 54 rotatably attached to the frame 40, 42, 44, 46. One or more of the towers 16, 18, 20, 22 may include a motor 56, 58, 60, 62 for driving the wheels 48, 50, 52, 54 of its respective tower 16, 18, 20, 22.

The conduit 14 spans across the irrigation system 10 and carries water and/or other fluids to the emitters 32. The conduit 14 may comprise piping, one or more hoses, or the like. Water and/or other fluids may travel from the water source 12 to the conduit 14, which directs them to the emitters 32.

The fluid emitters 32 apply the water and/or other fluids transported by the conduit 14 to the crops and/or soil beneath the conduit 14. The fluid emitters 32 are spaced along the truss sections 24, 26, 28, 30 and may include a plurality of sprayer heads, sprinkler drops, spray guns, drop nozzles, valves, and/or other devices.

The one or more valves 34 control flow of water and/or other fluids through the emitters 32. The valves 34 may be controllable via one or more actuators, such as pneumatic actuator, hydraulic actuators, mechanical actuators, solenoid-type actuators, or the like. The valves 34 may be binary, in that they only shut on or off, and/or the valves 34 may adjust a flow rate of the water and/or other fluids flowing through the conduit 14 and/or the emitters 32. The irrigation system 10 may comprise only one valve 34 that controls the flow of water and/or other fluids to/through the conduit 14. The irrigation system 10 may alternatively or additionally comprise a plurality of valves 34 for such control. For example, a valve 34 may be in fluid communication with each emitter 32 so that the valve 34 controls the flow of water and/or other fluids through its corresponding emitter 32.

The sensor 36 is configured to capture data about the field, climate, weather, soil, crops, or the like. In preferred embodiments, the sensor 36 is configured to capture soil data, such as a percentage of available water in the soil. The sensor 36 may comprise a time-domain reflectometry probe, a frequency-domain reflectometry sensor, a coaxial impedance dielectric reflectometry sensor, a gypsum block sensor, a neutron probe, or a gravimetric probe. The sensor 36 may be attached to the irrigation system 10 and/or installed at a location in the field.

The control system 38 is configured to control operations of the irrigation system 10. The control system 38 may comprise a communication element, a memory element, a processing element. The communication element may generally allow communication with systems or devices external to the control system 38. The communication element may include signal or data transmitting and receiving circuits, such as antennas, amplifiers, filters, mixers, oscillators, digital signal processors (DSPs), and the like. The communication element may establish communication wirelessly by utilizing RF signals and/or data that comply with communication standards such as cellular 2G, 3G, 4G, 5G, or LTE, WiFi, WiMAX, Bluetooth®, BLE, or combinations thereof. The communication element may be in communication with the processing element and the memory element.

The memory element may include data storage components, such as read-only memory (ROM), programmable ROM, erasable programmable ROM, random-access memory (RAM) such as static RAM (SRAM) or dynamic RAM (DRAM), cache memory, hard disks, floppy disks, optical disks, flash memory, thumb drives, universal serial bus (USB) drives, or the like, or combinations thereof. In some embodiments, the memory element may be embedded in, or packaged in the same package as, the processing element. The memory element may include, or may constitute, a "computer-readable medium". The memory element may store the instructions, code, code segments, software, firmware, programs, applications, apps, services, daemons, or the like that are executed by the processing element.

The processing element may include processors, microprocessors (single-core and multi-core), microcontrollers, DSPs, field-programmable gate arrays (FPGAs), analog and/or digital application-specific integrated circuits (ASICs), or the like, or combinations thereof. The processing element may generally execute, process, or run instructions, code, code segments, software, firmware, programs, applications, apps, processes, services, daemons, or the like. The processing element may also include hardware components such as finite-state machines, sequential and combinational logic, and other electronic circuits that can perform the functions necessary for the operation of the current invention. The processing element may be in communication with the other electronic components through serial or parallel links that include address busses, data busses, control lines, and the like.

Figure 2:
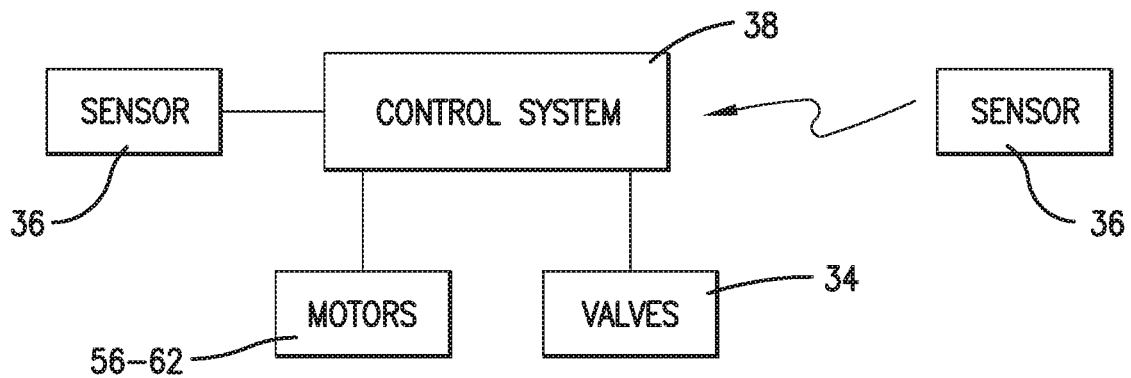
FIG. 2 is an elevated view of a field having exemplary different zones.

For example, the processing element of the control system 38 may be in communication with one or more of the valves 34, one or more of the sensors 36, and/or one or more of the motors 56, 58, 60, 62, as depicted in FIG. 2. The processing element may be in communication with the above components via the communication element and/or direct wiring. The processing element of the control system 38 may be configured to send and/or receive information to and/or from the above components. The processing element of the control system 38 may also be configured to send and/or receive a command to and/or from the above components.

The processing element of the control system 38 may be configured to determine a soil water depletion, or other attribute, at a first location in the field based on soil data from one or more of the sensors 36. The soil data may be received via wired or wireless communication, such as through the communication element of the control system 38. For example, one of the sensors 36 may be positioned to capture data representative of a percentage of available water at the first location. The sensor 36 may transmit the data through wired or wireless communication to the communication element of the control system 38 and/or another device that transmits the data to the communication element of the control system 38. The processing element may receive the data from the communication element.

The processing element may be configured to obtain from the memory element, or from an external database via wired or wireless communication, an available water holding capacity associated with the soil type at the first location. The processing element may also be configured to obtain from the memory element, or from an external database via wired or wireless communication, a root depth associated with a first crop located at the first location. The root depth associated with the first crop may be based, at least in part, on the estimated and/or calculated maturity of the crop. For example, the root depth may be based, at least in part, on a number of days remaining until relative maturity of the first crop, a number of days since planting the first crop, or a current growing degree unit (GDU) of the first crop. The number of days remaining and/or number of days since planting may be values that the processing element is configured to track and store in the memory unit and/or the values may be received from an external device/database or from a user. The current GDU of the first crop may likewise be calculated and/or tracked by the processing element. For example, the processing element may be configured to receive and/or sense various climate statistics associated with GDU. The processing element may be configured to calculate the GDU for the crop at the first location based on data, such as historic or similar data.

The processing element may be configured to determine the soil water depletion, and/or other data, at the first location, or where the sensor captured the data, based, at least in part, on the aforementioned data. For example, the processing element may be configured to calculate the soil water depletion at the first location according to Equation 1 below, wherein $Sensor_{dep}$ represents the soil water depletion (in millimeters(mm)) at the first location; $AW_{i,sensor}$ represents the percentage of available water at the first location captured by the sensor 36 on day (or other time interval) i, $AWHC_{sensor}$ represents the available water holding capacity associated with the soil type at the first location (in millimeters per meter(mm/m)), and $RD_i$ represent the root depth (in meters) of the soil for the crop at the first location at that crop's stage of maturity that day, or other time interval, i.

$$Sensor_{dep}=(1-AW_{i,sensor})\times AWHC_{sensor}\times RD_i \qquad (1)$$

Figure 3:
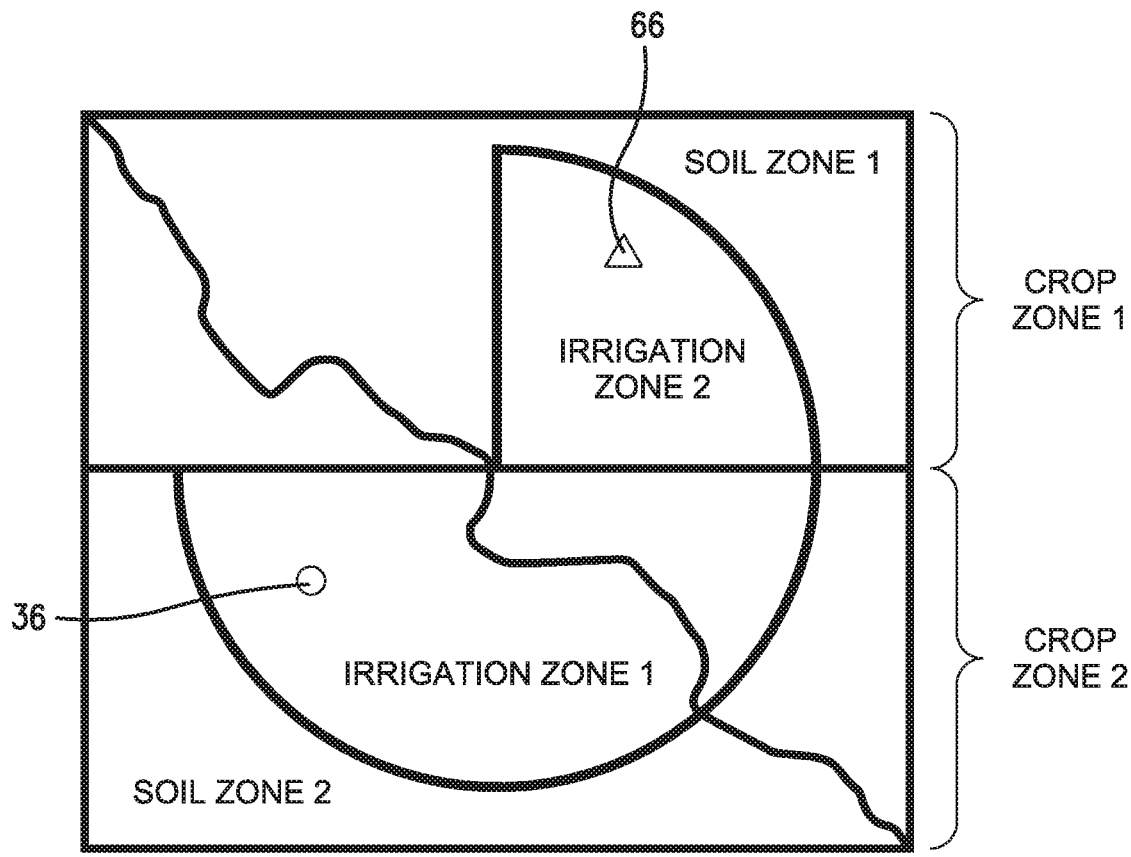
FIG. 3 is a block diagram depicting selected components of the irrigation system of FIG. 1.

The processing element of the control system 38 may be configured to calculate/interpolate data, such as an estimated soil water depletion, at one or more other locations 66 in the field. In some embodiments, the processing element of the control system 38 may interpolate the data, at least, for every location necessary to implement variable rate irrigation (VRI). The calculated/interpolated data may be based, at least in part, on the data captured by one or more of the sensors 36. For example, as depicted in FIG. 3, the field in which the irrigation system 10 travels may comprise a plurality of crop zones (each zone having an associated crop or crop type planted therein), a plurality of irrigation zones (each zone having a type of irrigation method applied), and/or a plurality of soil zones (each zone having a different type of soil). The sensor 36 may be located and capture data at the first location, which is in irrigation zone 1, soil zone 2, and crop zone 2. The soil water depletion, or other attribute, may be calculated, for example, at a second location 66 in irrigation zone 2, crop zone 1, and soil zone 1 using, at least in part, Equation 2 below, wherein $Zone_{dep}$ represents the soil water depletion (in mm) at the second location 66, Δirrigation represents the difference in irrigation amounts (in mm) between irrigation zone 1 and irrigation zone 2 since a baseline date (or during a time interval), Δrainfall represents the difference in rainfall amount (in mm) received between the first location where the sensor 36 is located and the second location 66, and $\Delta ET_c$ represents a difference in crop evapotranspiration values between the crops in crop zone 1 and the crops in crop zone 2 based on the crops respective maturities. The rainfall amount may be an effective precipitation amount that accounts for runoff from the surface of the soil.

$$Zone_{dep}=Sensor_{dep}-\Delta irrigation-\Delta rainfall+\Delta ET_c \qquad (2)$$

The processing element may be configured to receive and/or determine/calculate the values of Δirrigation, Δrainfall, and/or $\Delta ER_c$. The data relevant to calculating the values may be stored on the memory element and/or another database, which the processing element may be configured to receive via the communication element. For example, the processing element of the control system 38 may be configured to detect and track an irrigation amount for each irrigation zone and/or an amount of rainfall over each zone. Additionally, a crop type and corresponding evapotranspiration values may be entered into the control system 38 for each crop zone and stored on the memory element, which the processing element may be configured to access.

In some embodiments, the processing element of the control system 38 may further be configured to receive from the memory element and/or another database via the communication element a value representing a first capillary rise from groundwater table at the first location where the sensor 36 is located since the baseline date, or during the time interval. The processing element of the control system 38 may further be configured to receive from the memory element and/or another database via the communication element a value representing a second capillary rise from groundwater table at the second location 66 since the baseline date, or during the time interval. The processing element may be configured to determine a difference between the value representing the first capillary rise from groundwater table and the second capillary rise from groundwater table. Alternatively, the processing element may be configured to receive the difference from an external database. The processing element may be configured to account for this difference when determining/interpolating data, such as calculating the soil water depletion at the second location 66.

The processing element of the control system 38 may be further configured to calculate an estimated percentage of available soil water at the second location. For example, the processing element may use the corollary of Equation 1, which is shown as Equation 3 below, wherein $AW_{i,zone}$ zone represents the percentage of available water at the second location 66 that day, or other time interval, i, $AWHC_{zone}$ represents the available water holding capacity associated with the soil type at the second location 66 (in millimeters per meter), and $RD_{i,zone}$ represent the root depth (in meters) of the soil for the crop at the second location 66 at that crop's stage of maturity that day, or other time interval, i. The processing element may be configured to receive from the memory and/or another database an available water holding capacity associated with the second soil type at the second location 66. The processing element may receive from the memory element or another database a root depth associated with the crop located at the second location 66 based, at least in part, on a number of days remaining until relative maturity of the second crop in the second crop zone, a number of days since planting the second crop in the second crop zone, or a current growing degree unit of the second crop in the second crop zone.

$$AW_{i,zone} = 1 - \frac{Zone_{dep}}{AWHC_{zone} \times RD_{i,zone}} \quad (3)$$

The processing element of the control system 38 may be configured to store the detected/estimated soil water depletion of one or more locations 66 in the memory element and/or another database. The processing element may be configured to update the estimated soil water depletion after the time interval i (such as updating every day or prior to irrigation) based, at least in part, on new, updated data captured by the sensor 36 and/or according to Equation 4 below, wherein $D_i$ represents the relevant soil water depletion for time interval i, $D_{i-1}$ represents the relevant soil water depletion during the previous time interval i, $ET_{c,i}$ represents the relevant crop evapotranspiration on time interval i, $EP_i$ represents the effective precipitation on time interval i (accounting for runoff from the soil surface in some embodiments), $I_i$ represents the net irrigation depth applied on time interval i, and $CR_i$ represents the capillary rise from the groundwater table on time interval i.

$$D_i = D_{i-1} + ET_{c,i} - Ep_i - I_i - CR_i \quad (4)$$

The processing element of the control system 38 is configured to control one or more of the valves 34, one or more of the sensors 36, and/or one or more of the motors 56, 58, 60, 62 based, at least in part, on the estimated percentage of available soil water and/or the estimated soil water depletion at one or more locations 66 in the field. The processing element of the control system 38 may also use the data captured by the sensor 36 to control the application of water over the area where the sensor 36 is located. For example, if the processor element determines that the estimated soil water depletion at the second location 66 (or other locations/zones) is higher than an amount associated with the crop type at the location, then the processing element of the control system 38 may be configured to direct the valves 34 to remain open longer or be more open to allow more water to flow through the emitters when the irrigation system 10 is positioned over the second location 66. Alternatively or additionally, the processing element may be configured to direct the motors 56, 58, 60, 62 to operate slower or less frequently over that location 66 to allow for more water to be applied to that location 66. The processing element of the control system 38 may be configured to use the interpolated data to do this for every zone/location in the field so that each zone/location receives an amount of water consistent with the needs of the crop types (at its stage of growth during that irrigation cycle) in each zone. This reduces the amount of sensors needed, water waste, crop waste, and costs associated therewith.

EXAMPLE 1

A corn crop was planted in a section of a field (41.86220, −96.39132) on May 9, 2018 with a relative maturity value of 112 days and a GDUs to maturity value of 2800. The field had two soil zones: silty clay loam and sand. The sensor was installed in the silty clay loam at three depths, 30 centimeters (cm), 60 cm, and 1 meter (m). The sensor measured the currently available soil water is 80% of the available soil water. The water holding capacity is 200 mm/m and maximum rooting depth is 1 m. As a result, the soil water depletion of the sensor for this example, according to Equation 1, is 40 mm.

Assume for the sand soil zone that the same crop was planted on the same date as above (however, if different, this will change the interpolation as crop ET will be different) and the water holding capacity is 100 mm/m. Additionally, this area received a 30 mm irrigation event in a previous week, while the area with the soil moisture sensor received a 50 mm irrigation event in a previous week. No rainfall occurred during this time. As a result, the interpolated soil water depletion for the sand soil zone is 60 mm, according to Equation 2. Using Equation 3, the available water percentage is 40%.

Computer-Implemented Method Embodiment

Figure 4:
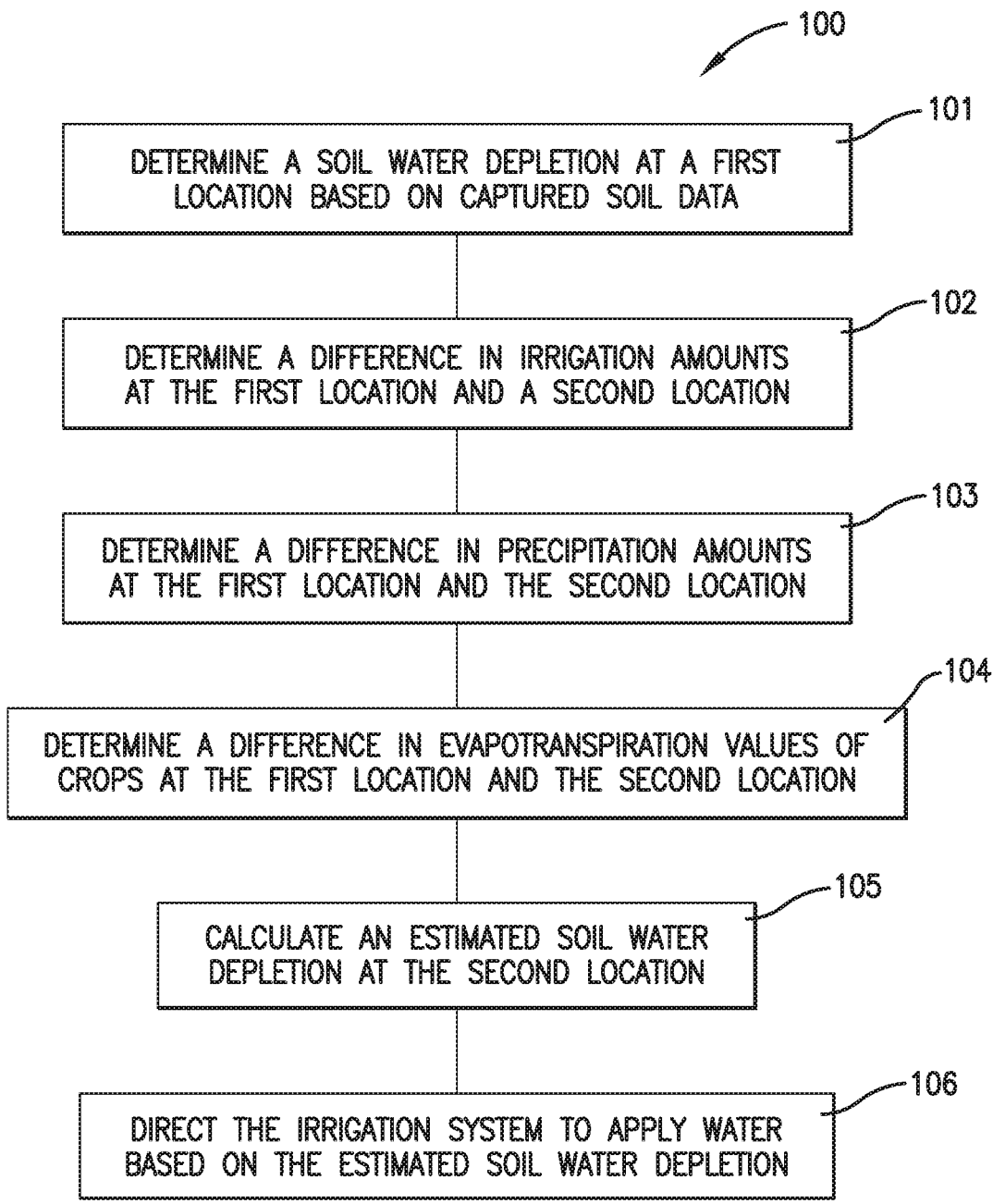
FIG. 4 is a flowchart depicting exemplary steps of a method according to an embodiment of the present invention.

The flow chart of FIG. 4 depicts the steps of an exemplary method 100 of controlling operations of an irrigation system. In some alternative implementations, the functions noted in the various blocks may occur out of the order depicted in FIG. 4. For example, two blocks shown in succession in FIG. 4 may in fact be executed substantially concurrently, or the blocks may sometimes be executed in the reverse order depending upon the functionality involved. In addition, some steps may be optional.

The method 100 is described below, for ease of reference, as being executed by exemplary devices and components introduced with the embodiments illustrated in FIGS. 1-3. The steps of the method 100 may be performed by the control system 38 through the utilization of processors, transceivers, hardware, software, firmware, or combinations thereof. However, some of such actions may be distributed differently among such devices or other devices without departing from the spirit of the present invention. Control of the system may also be partially implemented with computer programs stored on one or more computer-readable medium(s). The computer-readable medium(s) may include one or more executable programs stored thereon, wherein the program(s) instruct one or more processing elements to perform all or certain of the steps outlined herein. The program(s) stored on the computer-readable medium(s) may instruct processing element(s) to perform additional, fewer, or alternative actions, including those discussed elsewhere herein.

Referring to step 101, a soil water depletion, or other attribute, may be determined at a first location in the field. The soil water depletion may be determined via a control system based on soil data from one or more sensors. The soil data may be received via wired or wireless communication, such as through the communication element of the control system. For example, one of the sensors may be positioned to capture data representative of a percentage of available water at the first location. The data may be transmitted through wired or wireless communication to a communication element of the control system and/or another device that transmits the data to the communication element of the control system.

This step may include obtaining from the memory element, or from an external database via wired or wireless communication, an available water holding capacity associated with the soil type at the first location. A root depth associated with the first crop located at the first location may also be obtained. The root depth associated with the first crop may be based, at least in part, on the estimated and/or calculated maturity of the crop. For example, the root depth may be based, at least in part, on a number of days remaining until relative maturity of the first crop, a number of days since planting the first crop, or a current growing degree unit (GDU) of the first crop. The number of days remaining and/or number of days since planting may be values that are tracked and stored, via the processing element, in the memory unit and/or the values may be received from an external device/database or from a user. The current GDU of the first crop may likewise be calculated and/or tracked via the processing element. For example, various climate statistics associated with GDU may be received, via the control system. The GDU for the crop at the first location may be calculated, via the processing element or an external server, based on data, such as historic or similar data.

Referring to step 102, a difference in irrigation amounts at the first location and the second location is determined. The difference in irrigation amounts may comprise the difference in irrigation amounts (in mm) between irrigation zone 1 and irrigation zone 2 since a baseline date (or during a time interval). The data relevant to determining the difference may be stored on the memory element and/or another database, which may be received via the communication element of the control system. Alternatively, an irrigation amount for each irrigation zone may be detected and stored, via the control system.

Referring to step 103, a difference in precipitation amounts at the first location and the second location is determined. The difference in precipitation amounts may comprise the difference in rainfall amount (in mm) received between the first location where the sensor is located and the second location since a baseline date (or during a time interval). The rainfall amount may be an effective precipitation amount that accounts for runoff from the surface of the soil. The data relevant to determining the difference may be stored on the memory element and/or another database, which may be received via the communication element of the control system. Alternatively, a precipitation amount for each zone may be detected and stored, via the control system.

Referring to step 104, a difference in evapotranspiration values of crops at the first location and the second location is determined. The difference in evapotranspiration values may comprise the difference in crop evapotranspiration values between the crops in crop zone 1 and the crops in crop zone 2 based on their respective maturity. The data relevant to determining the difference may be stored on the memory element and/or another database, which may be received via the communication element of the control system. Alternatively, the evapotranspiration values for the crops/crop types of each zone may be detected and stored, via the control system.

Referring to step 105, an estimated soil water depletion at the second location is calculated based, at least in part, on the soil water depletion at the first location, the difference in irrigation amounts at the first location and the second location, the difference in precipitation amounts at the first location and the second location, and/or the difference in evapotranspiration values of crops at the first location and the second location. This step 105 may include calculating/interpolating data, such as an estimated soil water depletion, at one or more locations in the field. In some embodiments, the data may be interpolated, at least, for every location necessary to implement variable rate irrigation (VRI). The calculated/interpolated data may be based, at least in part, on the data captured by one or more of the sensors.

This step may further include receiving from the memory element and/or another database via the communication element a value representing a first capillary rise from groundwater table at the first location where the sensor is located since the baseline date, or during the time interval and receiving from the memory element and/or another database via the communication element a value representing a second capillary rise from groundwater table at the second location since the baseline date, or during the time interval. A difference between the value representing the first capillary rise from groundwater table and the second capillary rise from groundwater table may be determined and accounted for when calculating/interpolating data.

This step may also include calculating an estimated percentage of available soil water at the second location. An available water holding capacity associated with the second soil type at the second location may be received along with a root depth associated with the crop located at the second location based, at least in part, on a number of days remaining until relative maturity of the second crop in the second crop zone, a number of days since planting the second crop in the second crop zone, or a current growing degree unit of the second crop in the second crop zone.

Referring to step 106, the irrigation system is directed, via the control system, to apply an amount of water at the second location based, at least in part, on the estimated soil water depletion at the second location. For example, one or more of valves, one or more of sensors, and/or one or more of motors of the irrigation system may be controlled based, at least in part, on the estimated percentage of available soil water and/or the estimated soil water depletion at one or more locations in the field. This step may also include using the data captured by the sensor to control the application of water over the area where the sensor is located. For example, if the estimated soil water depletion at the second location (or other locations/zones) is determined to be higher than an amount associated with the crop type at the location, then the valves may be directed to remain open longer or be more open to allow more water to flow through the emitters when the irrigation system is positioned over the second location. Alternatively or additionally, the motors may be directed to operate slower or less frequently over the second location to allow for more water to be applied to the second location. The interpolated data may be used to do this for every zone/location in the field so that each zone/location receives an amount of water consistent with the needs of the crop types (at its stage of growth during that irrigation cycle) in each zone.

The method 100 may include additional, less, or alternate steps and/or device(s), including those discussed elsewhere herein. For example, the detected/estimated soil water depletion of one or more locations may be stored or tracked in the memory element and/or another database. The estimated soil water depletion may be updated after the time interval (such as updating every day or prior to irrigation) based, at least in part, on new, updated data captured by the sensor and/or according to Equation 4 above.

Although the invention has been described with reference to the embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

The invention claimed is:

1. A computer-implemented method of controlling operations of an irrigation system, the computer-implemented method comprising:
   determining, via a control system, a soil water depletion at a first location based on soil data captured via a sensor;
   determining, via the control system, a difference in irrigation amounts at the first location and a second location;
   determining, via the control system, a difference in precipitation amounts at the first location and the second location;
   determining, via the control system, a difference in evapotranspiration values of crops at the first location and the second location;
   calculating an estimated soil water depletion at the second location based, at least in part, on the soil water depletion at the first location, the difference in irrigation amounts at the first location and the second location, the difference in precipitation amounts at the first location and the second location, and the difference in evapotranspiration values of crops at the first location and the second location; and
   directing, via the control system, the irrigation system to apply an amount of water at the second location based, at least in part, on the estimated soil water depletion at the second location.

2. The computer-implemented method of claim 1, further comprising receiving, via the control system, the soil data from the sensor, wherein the soil data comprises a percentage of available water at the first location.

3. The computer-implemented method of claim 2, wherein the step of determining the soil water depletion comprises
   receiving from a database, via the control system, a first available water holding capacity associated with a first soil type at the first location; and
   receiving from the database, via the control system, a first root depth associated with a first crop located at the first location based, at least in part, on at least one of a number of days remaining until relative maturity of the first crop, a number of days since planting the first crop, or a current growing degree unit of the first crop.

4. The computer-implemented method of claim 1, further comprising
   receiving from a database, via the control system, an available water holding capacity associated with a soil type at the second location;
   receiving from the database, via the control system, a root depth associated with a crop located at the second location based, at least in part, on at least one of a number of days remaining until relative maturity of the second crop, a number of days since planting the second crop or a current growing degree unit of the second crop; and
   determining an estimated percentage of available soil water at the second location based on, at least in part, the available water holding capacity associated with the soil type at the second location, the root depth associated with the crop located at the second location, and the estimated soil water depletion,
   wherein the step of directing the irrigation system includes directing the irrigation system to apply the amount of water at the second location based, at least in part, on the estimated percentage of available soil water at the second location.

5. The computer-implemented method of claim 1, wherein the step of determining the difference in irrigation amounts includes receiving from a database, via the control system, a first amount of irrigation depth applied at the first location during a time interval and a second amount of irrigation depth applied at the second location during the time interval.

6. The computer-implemented method of claim 1, wherein the step of determining the difference in precipitation amounts includes receiving from a database, via the control system, a first effective precipitation at the first location since a time interval and a second effective precipitation at the second location since the time interval.

7. The computer-implemented method of claim 6, wherein the first effective precipitation and the second effective precipitation account for soil surface runoff.

8. The computer-implemented method of claim 1, wherein the step of calculating the estimated soil water depletion at the second location includes
   receiving from a database, via the control system, a first capillary rise from groundwater table at the first location since a time interval and a second capillary rise from groundwater table at the second location since the time interval; and
   determining, via the control system, a difference between the first capillary rise from groundwater table and the second capillary rise from groundwater table.

9. The computer-implemented method of claim 1, further comprising storing, via the control system, the estimated soil water depletion in a database.

10. The computer-implemented method of claim 9, further comprising receiving from the database, via the control system, the estimated soil water depletion and determining a new estimated soil water depletion based, at least in part, on the estimated soil water depletion.

11. An irrigation system comprising:
- a plurality of mobile support towers configured to move across a field, one or more of the support towers having a motor;
- a fluid-carrying conduit supported above the field by the mobile towers;
- water emitters coupled with the fluid-carrying conduit;
- at least one valve for controlling flow of fluids through the water emitters;
- a sensor configured to capture soil data at a first location in the field; and
- a control system configured to
  - determine a soil water depletion at the first location in the field based on the soil data;
  - determine a difference in irrigation amounts at the first location and a second location;
  - determine a difference in precipitation amounts at the first location and the second location;
  - determine a difference in evapotranspiration values of crops at the first location and the second location;
  - calculate an estimated soil water depletion at the second location based, at least in part, on the soil water depletion at the first location, the difference in irrigation amounts at the first location and the second location, the difference in precipitation amounts at the first location and the second location, and the difference in evapotranspiration values of crops at the first location and the second location; and
  - control operation of the motor and/or the valve to apply an amount of water at the second location based, at least in part, on the estimated soil water depletion at the second location.

12. The irrigation system of claim 11, wherein the control system is configured to control operation of the motor and/or the valve to apply an amount of water at the first location based, at least in part, on the soil water depletion at the first location.

13. The irrigation system of claim 11, wherein the sensor is configured to detect a percentage of available water at the first location.

14. The irrigation system of claim 11, wherein the sensor comprises at least one of a time-domain reflectometry probe, a frequency-domain reflectometry sensor, a coaxial impedance dielectric reflectometry sensor, a gypsum block sensor, a neutron probe, or a gravimetric probe.

15. A computer-implemented method of controlling operations of an irrigation system in a field having a first soil type, a second soil type, a first irrigation zone, a second irrigation zone, a first crop zone, and a second crop zone, the computer-implemented method comprising:
- sensing, via a sensor, a first percentage of available soil water in the first soil type at a first location in the first irrigation zone and first crop zone;
- receiving, via a control system, a first available water holding capacity associated with the first soil type from a database;
- receiving from the database, via the control system, a first root depth associated with the first crop zone based, at least in part, on at least one of a number of days remaining until relative maturity of a first crop in the first crop zone, a number of days since planting the first crop in the first crop zone, or a current growing degree unit of the first crop in the first crop zone;
- receiving, via the control system, a second available water holding capacity associated with the second soil type from a database;
- receiving from the database, via the control system, a second root depth associated with the second crop zone based, at least in part, on at least one of a number of days remaining until relative maturity of a second crop in the second crop zone, a number of days since planting the second crop in the second crop zone, or a current growing degree unit of the second crop in the second crop zone;
- determining, via the control system, an estimated percentage of available soil water at a second location that has the second soil type and that is in the second irrigation zone and the second crop zone based, at least in part, on the first percentage of available soil water, the first available water holding capacity, the first root depth, the second available water holding capacity, and the second root depth;
- directing the irrigation system, via the control system, to apply an amount of water at the first location based, at least in part, on the first percentage of available soil water; and
- directing the irrigation system, via the control system, to apply an amount of water at the second location based, at least in part, on the estimated percentage of available soil water.

16. The computer-implemented method of claim 15, wherein the step of determining the estimated percentage of available soil water includes
- receiving from the database, via the control system, a first amount of irrigation depth applied at the first location during a time interval and a second amount of irrigation depth applied at the second location during the time interval;
- determining, via the control system, a first difference between the first amount and the second amount;
- receiving from the database, via the control system, a first evapotranspiration value associated with at least one of the number of days remaining until relative maturity of the first crop in the first crop zone, the number of days since planting the first crop in the first crop zone, or the current growing degree unit of the first crop in the first crop zone;
- receiving from the database, via the control system, a second evapotranspiration value associated with at least one of the number of days remaining until relative maturity of the second crop in the second crop zone, the number of days since planting the second crop in the second crop zone, or the current growing degree unit of the second crop in the second crop zone;
- determining, via the control system, a second difference between the first evapotranspiration value and the second evapotranspiration value; and
- determining, via the control system, the estimated percentage of available soil water at the second location based, at least in part, on the first difference and the second difference.

17. The computer-implemented method of claim 15, wherein the step of determining the estimated percentage of available soil water includes
- receiving from the database, via the control system, a first effective precipitation at the first location during a time interval and a second effective precipitation at the second location during the time interval;
- determining, via the control system, a third difference between the first effective precipitation and the second effective precipitation; and determining, via the control system, the estimated percentage of available soil water at the second location based, at least in part, on the third difference.

18. The computer-implemented method of claim 15, wherein the step of determining the estimated percentage of available soil water includes receiving from the database, via the control system, a first capillary rise from groundwater table at the first location during a time interval and a second capillary rise from groundwater table at the second location during the time interval;

determining, via the control system, a fourth difference between the first capillary rise from groundwater table and the second capillary rise from groundwater table; and determining, via the control system, the estimated percentage of available soil water at the second location based, at least in part, on the fourth difference.

19. The computer-implemented method of claim 15, further comprising storing, via the control system, the estimated percentage of available soil water in the database.

20. The computer-implemented method of claim 19, further comprising receiving from the database, via the control system, the estimated percentage of available soil water and determining, via the control system, a new estimated percentage of soil water based, at least in part, on the estimated percentage of available soil water.

\* \* \* \* \*